US005641502A

United States Patent [19]
Skalla et al.

[11] Patent Number: 5,641,502
[45] Date of Patent: Jun. 24, 1997

[54] BIODEGRADABLE MOLDABLE SURGICAL MATERIAL

[75] Inventors: Walter Skalla, East Haven; Steven L. Bennett, New Haven; Ying Jiang, North Haven, all of Conn.

[73] Assignee: United States Surgical Corporation, Norwalk, Conn.

[21] Appl. No.: 480,084

[22] Filed: Jun. 7, 1995

[51] Int. Cl.⁶ ............................. A61F 2/00; A61L 15/64
[52] U.S. Cl. .................................. 424/426; 424/486
[58] Field of Search .......................... 424/426, 502, 424/486

[56] References Cited

U.S. PATENT DOCUMENTS

| | | | |
|---|---|---|---|
| 3,773,919 | 11/1973 | Boswell et al. | 424/486 |
| 3,919,163 | 11/1975 | Clendinning et al. | 260/40 R |
| 4,027,676 | 6/1977 | Mattei | 128/335.5 |
| 4,440,789 | 4/1984 | Mattei et al. | 528/354 |
| 4,595,713 | 6/1986 | St. John | 523/105 |
| 4,624,256 | 11/1986 | Messier et al. | 128/335.5 |
| 4,702,917 | 10/1987 | Schindler | 424/422 |
| 4,716,203 | 12/1987 | Casey et al. | 525/408 |
| 4,745,160 | 5/1988 | Churchill et al. | 525/415 |
| 4,837,381 | 6/1989 | Steber et al. | 424/502 |
| 5,080,665 | 1/1992 | Jarrett et al. | 606/219 |
| 5,123,912 | 6/1992 | Kaplan et al. | 606/230 |
| 5,143,730 | 9/1992 | Fues et al. | 424/426 |
| 5,308,623 | 5/1994 | Fues et al. | 424/426 |
| 5,312,437 | 5/1994 | Hermes et al. | 606/239 |

OTHER PUBLICATIONS

Chem. Ab. vol. 124:15342 McGinty et al Eur. J. Pharm. Biopharm. (1994) 40(6) 355–63.

Primary Examiner—Peter F. Kulkosky

[57] ABSTRACT

A moldable biodegradable surgical material is made of a bioabsorbable polymer derived from hydroxyacids, tactones, carbonates, etheresters, anhydrides, orthoesters and copolymers, terpolymers and/or blends thereof, the polymer blended with at least one surface active agent selected from the group consisting of fatty acid ester and poly(oxypropylene)/poly(oxyethylene) block copolymer. In one embodiment, a leaching agent is blended with the above-mentioned surgical material. Methods of making moldable biodegradable surgical material are provided. The surgical material may be used as a moldable bone wax in connection with repair of wounds and is an adaptable aid for any appropriate surgical use, e.g., hemostat, anchor, patch etc.

16 Claims, No Drawings

BIODEGRADABLE MOLDABLE SURGICAL MATERIAL

BACKGROUND

1. Technical Field

The present disclosure relates to implantable moldable biodegradable polymeric materials used in medicine for surgical repair.

2. Background of Related Art

Biodegradable materials are used in medicine for a variety of purposes including drug delivery devices and as aids in tissue repair. Physical and chemical properties of such materials can vary as in the case of different polymeric materials, e.g., melting point, degradation rate, stiffness, etc. The variability in physical and chemical properties allows products made from such materials to be tailored to suit specific applications.

Absorbable sutures can be made from biodegradable polymers such as glycolide and lactide. Biodegradable polymers can be used to coat sutures, e.g., U.S. Pat. No. 4,624,256 is directed to caprolactone polymers for suture coating. As described therein, the coating contains high molecular weight polycaprolactone or a high molecular weight copolymer of at least 90% by weight of caprolactone and at most 10% by weight of another biodegradable monomer such as glycolide and lactide. The high molecular weight polycaprolactone may be mixed with up to 50% by weight of lubricating agents which include poly(ethylene oxide).

A resorbable bone wax is described in U.S. Pat. No. 5,143,730. The bone wax is said to be suitable for mechanical staunching of blood on hard body tissue and is based on oligomers of glycolic acid and/or lactic acid with monofunctional and/or polyfunctional alcohols and/or corresponding carboxylic acids. A content of body-compatible salts of organic and/or inorganic acids is said to be formed by the reaction of any free carboxyl groups. Glycerol or glycerol partial esters are used to regulate the average molecular weight of the oligomer fraction.

U.S. Pat. No. 4,440,789 is directed to synthetic absorbable hemostatic composition. As described therein, a semisolid bone sealant contains between about 65% and 85% by weight of polydioxanone in a base which may contain ethylene/propylene oxide block copolymers, polyethylene glycols or methoxypolyethylene glycols. U.S. Pat. No. 5,080,665 is directed to a deformable absorbable surgical device manufactured from a block or graft copolymer. The copolymer is described as having a plurality of first linkages selected from the group consisting of glycolic acid ester and lactic acid ester linkages and a plurality of second linkages selected from the group consisting of 1,3 dioxane-2-one; 1,4-dioxane-2-one and ε-caprolactone linkages. A deformable surgical repair device is described as being manufactured from a blend of a first and second absorbable polymer, the first polymer corresponding to the first above linkages and the second polymer corresponding to the second above linkages.

Medical putty for tissue augmentation is described in U.S. Pat. No. 4,595,713 and is said to be useful in the regeneration of soft and hard connective tissue. As described therein, an implant material is composed of a copolymer of 60–95% epsilon caprolactone and 40–5% lactide. Catalysts used for the copolymer are metallic esters of carboxylic acids. The polymer is said to become moldable at hot water temperatures of about 115°–160° F.

SUMMARY

A moldable biodegradable surgical material is made of a bioabsorbable polymer derived from at least one of hydroxyacids, lactones, carbonates, etheresters, anhydrides, orthoesters and copolymers, terpolymers and/or blends thereof, the polymer blended with a surface active agent of at least one sorbitan fatty acid ester and/or a poly (oxypropylene) block polymer with poly(oxyethylene). In one embodiment, the bioabsorbable polymer is present in an amount ranging from about 30 percent to about 90 percent by weight of the biodegradable surgical material and the sorbitan fatty acid ester is present in an amount ranging from about 10 percent to about 70 percent by weight of the biodegradable surgical material. In another embodiment, the bioabsorbable polymer is present in an amount ranging from about 45 percent to about 80 percent by weight of the biodegradable surgical material and the poly(oxypropylene) block copolymer with poly(oxyethylene) is present in an amount ranging from about 2 percent to about 55 percent by weight of the biodegradable surgical material. In another embodiment, a leaching agent is blended with the above-mentioned biodegradable surgical material to form another surgical material. Methods of making moldable biodegradable surgical material are provided. In another embodiment, a moldable biodegradable surgical material includes a bioabsorbable polymer as described above blended with a leaching agent.

The biodegradable surgical material may be used as a moldable bone wax in connection with repair of wounds. The moldable, biodegradable nature of the implantable surgical material allow it to be shaped to fit underlying or overlying interior terrain of the body. The biodegradable surgical material is thus an adaptable aid for any appropriate surgical use, e.g., hemostat, anchor, patch, etc.

DETAILED DESCRIPTION OF PREFERRED EMBODIMENTS

A biodegradable moldable polymeric surgical material (hereinafter "surgical material") as described herein is adaptable for many uses in vivo. The surgical material is implanted and allowed to resorb in place while acting as a hemostat, anchor and/or patch. The surgical material provides excellent moldability and workability at both room and body temperatures and good stability in vivo during the applicable healing period. As a bone wax, after being molded to a desired shape, the surgical material maintains that shape for a prolonged period and is resilient to deformation under normal interior body conditions to provide durable coverage of the intended locus.

In one aspect, the surgical material is made of a biodegradable polymer which is a biocompatible, hydrolyzable material derived from any of the following: hydroxyacids, lactones, carbonates, etheresters, arthydrides, esteramides, orthoesters, and copolymers, terpolymers, and/or blends thereof.

Such materials include but are not limited to hydroxyacid derivatives such as glycolide, lactide, butyrates and valerates; carbonates such as trimethylene carbonate and hexamethylene carbonate; lactones such as caprolactone and dioxanone; and various combinations of these and related monomers. Polymers, copolymers, block copolymers, and blends of the afore-mentioned materials are known in the art and are disclosed, e.g., in U.S. Pat. Nos. 2,668,162; 2,703, 316; 2,758,987; 3,225,766; 3,297,033; 3,422,181; 3,531, 561; 3,565,077; 3,565,869; 3,620,218; 3,626,948; 3,636, 956; 3,736,646; 3,772,420; 3,773,919; 3,792,010; 3,797, 499; 3,839,297; 3,867,190; 3,878,284; 3,982,543; 4,047,533; 4,060,089; 4,137,921; 4,157,437; 4,234,775; 4,237,920; 4,300,565; 4,523,591; 4,916,193; and 5,120,802; U.K. Patent No. 779,291; D. K. Gliding et al., "Biodegradable polymers for use in surgery-polyglycolic/poly(lactic acid) homo- and co-polymers": 1, Polymer, Volume 20, pages 1459–1464 (1979), and D. F. Williams (ed.), Biocompatibility of Clinical Implant Materials, Vol. II, ch. 9: "Biodegradable Polymers" (1981), which are hereby incorporated by reference. Preferred polymers for use in making the surgical material are glycolide, lactide, polycaprolactone, trimethylene carbonate and dioxanone.

In a preferred embodiment the biodegradable polymer is made of a major amount of ε-caprolactone and a minor amount of a monomer which may be one or more hydroxyacids, lactones, carbonates and/or mixtures thereof. The polymer is obtained by polymerizing a major amount of ε-caprolactone and a minor amount of at least one of the above copolymerizable monomers or mixture of such monomers in the presence of a monofunctional initiator or a polyfunctional initiator such as a polyhydric alcohol initiator. Use of a polyfunctional initiator results in formation of a star polymer. The polymerization of these monomers contemplates all of the various types of monomer addition, i.e., simultaneous, sequential, simultaneous followed by sequential, sequential followed by simultaneous, etc.

Suitable monomers which can be copolymerized with ε-caprolactone include all the known hydroxyacids, lactones and carbonates that, when polymerized, are capable of biodegradation, e.g., glycolide, lactide, p-dioxanone, trimethylene carbonate and the like.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N,N',N'-tetrakis(2-hydroxypropyl)ethylenediamine, dipentaerythritol, allitol, dulcitol, glycitol, altritol, iditol, sorbitol, mannitol, inositol, and the like.

The biodegradable polymer herein can contain from about 85 to about 100, and preferably greater than about 90, weight percent ε-caprolactone-derived units, the balance of the copolymer being derived from the other copolymerizable monomer(s). The molecular weight of the biodegradable polymer ranges from about 2,000 to about 30,000 and the inherent viscosity of the biodegradable polymer generally ranges from about 0.10 to about 0.60, and preferably from about 0.20 to about 0.50, dl/g when measured in chloroform at a concentration of 0.2500 g/dl at 30° C. The polyhydric alcohol initiator, e.g., mannitol is generally employed in small amounts, e.g., from about 0.5 to about 5, and preferably from about 0.1 to about 2, weight percent of the total monomer mixture. In one embodiment, ε-caprolactone is present in an amount of about 90.2 weight percent and glycolide is present in an amount of about 9.8 weight percent of the biodegradable polymer.

In another embodiment, the biodegradable polymer is a block copolymer made of about 25 to about 75 weight percent of a block having about 10 to about 35 weight percent glycolide and about 65 to about 90 weight percent lactide and about 25 to about 75 weight percent of a block having polyethylene oxide. The molecular weight of polyethylene oxide may range from about 1,000 to about 10,000. Such a polymer is described in U.S. Pat. No. 5,123,912, herein incorporated by reference. In yet another aspect, the biodegradable polymer is a block copolymer made of about 25 to about 75 weight percent of a block having about 10 to about 35 weight percent glycolide and about 65 to about 90 weight percent lactide and about 25 to about 75 weight percent of a block having polypropylene oxide. The molecular weight of polypropylene oxide may range from about 400 to about 6000. Such a polymer is described in U.S. Pat. No. 5,312,437, herein incorporated by reference.

Any of the biodegradable polymers mentioned above are blended, either alone or in combination, with a surface active agent. In one embodiment, about 10 percent to about 70 percent by weight of at least one sorbitan fatty acid ester is used to manufacture the surgical material. In a preferred embodiment, the sorbitan fatty acid ester is present in an amount ranging from about 35 percent to about 50 percent by weight of the surgical material. The biodegradable polymer and the sorbitan fatty acid ester are blended by conventional techniques known in the art.

Sorbitan fatty acid ester surface active agents may be derived from the hexahydroxy alcohol sorbitol, which on dehydration forms a mixture of five- and six-membered rings called sorbitan. Esterification of the primary hydroxyl group with lauric, palmitic, stearic, or oleic acid forms sorbitan monolaurate, monopalmitate, monostearate or monoleate, water insoluble nonionic surfactants commercially available as Span® 20, 40, 60, or 80, respectively. Addition of about 20 ethylene oxide molecules produces a water soluble surfactant which may be known as polysorbate. Examples of such water soluble sorbitan fatty acid esters are polyoxyethylene sorbitan monolaurate (commercially available as Tween® 20), polyoxyethylene sorbitan monopalmitate (commercially available as Tween® 40), polyoxyethylene sorbitan monostearate (commercially available as Tween® 60), polyoxyethylene sorbitan monoleate (commercially available as Tween® 80) and polyoxyethylene sorbitan trioleate (commercially available as Tween® 85). A preferred sorbitan fatty acid ester is Tween® 40.

In another embodiment, any of the above-mentioned biodegradable polymers are blended, either alone or in combination, with about 2 percent to about 55 percent by weight of a poly(oxypropylene) block polymer with poly(oxyethylene) surface active agent. Such poly(oxypropylene)/poly(oxyethylene) block copolymers are biocompatable and biodegradable and combine, as described below, with the biodegradable polymers to form materials of excellent moldability and workability. Preferred poly(oxypropylene)/poly(oxyethylene) block copolymers may be liquid or solid. Poly(oxypropylene/poly(oxyethylene) block copolymers are commercially available from BASF Corporation under the tradename Pluronic®. Examples of suitable Pluronics® include those designated L64 (molecular weight about 2900), F68LF (molecular weight about 7500), F68 (molecular weight about 8350), F68CS (molecular weight about 8400), and F77 (molecular weight about 6600). The biodegradable polymer and the poly(oxypropylene)/poly(oxyethylene) block copolymers are blended by conventional techniques known in the art.

In one embodiment, at least one leaching agent is blended with the above described materials to provide a porous microstructure which is formed as the leaching agent clears out of the surgical material. The resulting porous microstructure allows and encourages bone ingrowth through the interstices created where the leaching agent formerly occupied space. Additionally, incorporation of one or more leaching agents reduces tackiness and improves workability and moldability of the surgical material. Suitable leaching agents include calcium carbonate, calcium chloride, tricalcium phosphate and hydroxyapatite. The amount of leaching agent ranges from about 0 weight percent to about 70 weight percent of the surgical material.

In another embodiment, a moldable biodegradable surgical material includes a bioabsorbable polymer as described above and a leaching agent as described above. The amount of leaching agent may range from about 1 weight percent to about 70 weight percent of the surgical material.

The biodegradable moldable surgical material is non-toxic and physiologically inert. Depending on its particular physical and bioabsorption properties, which are influenced to a large extent by the relative amounts of polymer and surface active agent, the surgical material can be applied as a bone wax to prevent or stop osseous hemorrhage or as a patch to fill voids or as an anchor for loose tissue and/or other surgical aids such as sutures, fasteners and the like. Increasing the percentage of the surface active agent in the surgical material increases softness and allows the material to be molded more easily. The surgeon may optionally heat the material to slightly above ambient temperature to a temperature of about 40° C. to facilitate moldability. The material may be heated, kneaded and/or shaped by the surgeon to fit a target terrain and applied to the appropriate locus for the desired affect. The material may be loaded into a syringe and extruded into a desired locus. Such use is suitable for hard to reach areas such as those that are attendant to dental or maxillofacial surgery.

The following examples are included for purposes of illustration and are not intended to limit the disclosure herein.

EXAMPLE 1

Dry glycolide (300.0 gm), ε-caprolactone (2760 gm), stannous octoate as catalyst (0.3 gm) and dry mannitol as initiator (39.0 gm) were mixed under $N_2$ for one hour. The mixture was heated in a reactor at a temperature of 160° C. for 24 hours. Greater than 95 percent conversion of monomers to copolymer was obtained. The polymer has a molecular weight of about 14,000.

EXAMPLE 2

In a dry room, distilled glycolide (30 gm), ε-caprolactone (270 gm), stannous octoate as catalyst (0.06 gm) and dry mannitol as initiator (1.95 gm) were added to a 500 ml round bottom flask that has been dried with nitrogen gas. The flask, containing a mechanical stirrer, was placed in an oil bath and heated to 160° C. ±3 in approximately 3 hours, and kept at 160° C. for 24 hours while mixing under a static nitrogen gas flow. The contents of the flask were placed in a vacuum oven, post-treated at 120° C. for 24 hours and then moved to a dry room. The polymer was designated Polymer A and had a molecular weight of about 28,000.

EXAMPLE 3

25.0 gm of Polymer A from Example 2 and 20.45 gm of Tween® 40 along with a stir bar were added to a heat dried 250 ml flask. The flask was placed in an oil bath at 160° C. for 4 hours under static nitrogen gas. The polymer melted into a liquid which was stirred and then allowed to cool and solidify in a dry room. The resulting product was a hand moldable material having 55/45 Polymer A/Tween®40 by weight.

EXAMPLE 4

15.0 gm of Polymer A from Example 2 and 12.2 gm of Tween® 40 along with a stir bar were added to a clean 100ml round bottom flask. A static nitrogen gas line was added and the flask was placed in an oil bath at 160° C. for 3 hours. The polymer melted into a liquid which was stirred and then allowed to cool in a dry room overnight. The resulting product was a hand moldable material having 55/45 Polymer A/Tween® 40 by weight.

EXAMPLE 5

15.0 gm of Polymer A from Example 1 and 10gm of Tween® 40 along with a stir bar were added to a clean 100 ml round bottom flask. A static nitrogen gas line was added and the flask was placed in an oil bath at 160° C. for 3 hours. The contents of the flask were not stirred for the first three hours. The contents were then stirred overnight at 150° C. The resulting product was a hand moldable material having 60/40 Polymer A/Tween® 40 by weight.

EXAMPLE 6

Approximately 1 gm of the product of Example 4 was mixed in a 1:1 ratio by weight with fine grain tricalcium phosphate (TCP) commercially available from Hitempco Medical Applications, Inc. The product and TCP were mixed by triturating with a spatula. The resulting product was placed in a dry room for 24 hours. The resulting product exhibited good moldability by hand.

EXAMPLE 7

Approximately 1 gm of the product of Example 4 was mixed in a 2:1 ratio by weight with fine grain tricalcium phosphate (TCP) commercially available from Hitempco Medical Applications, Inc. The product and TCP were mixed by triturating with a spatula. The resulting product was placed in a dry room for 24 hours. The resulting product exhibited good moldability by hand.

EXAMPLE 8

Approximately 1 gm of product of Example 5 that had not yet completely solidified was mixed in a 3:2 ratio by weight with fine grain tricalcium phosphate commercially available from Hitempco Medical Applications, Inc. The product and TCP were mixed by triturating with a spatula. The resulting product was placed in a dry room for 24 hours. The resulting product was harder and less moldable than the products of Examples 6 and 7 above.

EXAMPLE 9

Approximately 1 gm of product of Example 5 that had not yet completely solidified was mixed in a 1:1 ratio by weight with fine grain tricalcium phosphate commercially available from Hitempco Medical Applications, Inc. The product and TCP were mixed by triturating with a spatula. The resulting product was placed in a dry room for 24 hours. The resulting product was harder and less moldable than the products of Examples 6 and 7 above.

EXAMPLE 10

Approximately 1 gm of product of Example 5 was mixed in a 2:1 ratio by weight with fine grain tricalcium phosphate commercially available from Hitempco Medical Applications, Inc. The product and TCP were mixed by triturating with a spatula. The resulting product was placed in a dry room for 24 hours. The resulting product was moldable by hand and slightly stickier than the product of Example 7 above.

EXAMPLE 11

In a dry room glycolide (30 gm), ε-caprolactone (270 gm), stannous octoate as catalyst (0.06 gm) and dry mannitol as initiator (3.9 gm) were added to a 500 ml round bottom flask dried with nitrogen gas. The flash, containing a mechanical stirrer, was placed in an oil bath at 160° C.±3 for approximately 24 hours and mixed under a static nitrogen gas flow. The contents of the flask were placed into a dry room. The polymer was designated Polymer B and had a molecular weight of about 14,000.

EXAMPLE 12

10 gm of Polymer B from Example 11 and 7.39 gm of Tween® 40 along with a stir bar were added to a clean 100 ml round bottom flask. A static nitrogen gas line was added to the flask and the flask was placed in an oil bath at 160° C. for 4 hours. The polymer melted into a liquid which was stirred and then allowed to cool in a dry room overnight. The resulting product was a hand moldable surgical material having 57.5/42.5 Polymer B/Tween® 40 by weight. The product was slightly softer and stickier than products incorporating Polymer A.

EXAMPLE 13

11.25 gm of Polymer B from Example 11 and 13.75 gm of Tween® 40 along with a stir bar were added to a clean 100 ml round bottom flask. A static nitrogen gas line was added to the flask and the flask was placed in an oil bath at 160° C. for 5 hours. The polymer melted into a liquid that was stirred and then allowed to cool in a dry room. The resulting material had 45/55 Polymer B/Tween® 40 by weight and was soft. 12.5 gm fine grain tricalcium phosphate was added to the product by triturating with a spatula. The resulting product was moldable by hand and was slightly sticky.

EXAMPLE 14

13.75 of Polymer B from Example 11 and 11.25 gm Tween® 40 along with a stir bar were added to a clean 100 ml round bottom flask. A static nitrogen gas line was added to the flask and the flask was placed in an oil bath at between 160° C. to 170° C. for 5 hours. The polymer melted into a liquid that was stirred and allowed to cool in a dry room. The resulting material had 55/45 Polymer B/Tween®40 by weight but was too hard to be moldable by hand. 12.5 gm fine grain tricalcium phosphate (Hitempco Medical Applications, Inc.) was mixed into the material by triturating with a spatula. The resulting product was moldable by hand.

EXAMPLE 15

5 gm of Polymer B from Example 11 was placed in a flask and heated in a vacuum oven at 107° C. under static nitrogen gas until it melted. The contents of the flask were transferred to a scintillation vial along with 7.5 gm of liquid Tween® 40. The contents were mixed by hand. The resulting product was very thin and difficult to work with.

EXAMPLE 16

5 gm of Polymer B from Example 11 was placed in a flask and heated in a vacuum oven at 107° C. under static nitrogen gas until it melted. The contents of the flask were transferred to a scintillation vial along with 11.67 gm of liquid Tween® 40. The contents were mixed by hand. The resulting product was difficult to mix due to the high concentration of Tween® 40 and did not form a homogenous mixture.

EXAMPLE 17

5 gm of Polymer B from Example 11 was placed in a flask and heated in a vacuum oven at 107° C. under static nitrogen gas until it melted. The contents of the flask were transferred to a scintillation vial along with 5 gm of liquid Tween® 40. The contents were mixed by hand. The resulting product hardened into a hand moldable material that became thin and sticky after continued kneeding.

EXAMPLE 18

10 gm of Polymer B from Example 11 and 10 gm of Tween® 40 along with a stir bar were added to a clean 100 ml round bottom flask. A static nitrogen gas line was added to the flask and the flask was placed in an oil bath at 160° C. for 4 hours. The polymer melted into a liquid that was stirred and then allowed to cool overnight in a dry room. The resulting product hardened into a hand moldable material that became thin and sticky after continued kneading.

EXAMPLE 19

5 gm of the product of Example 18 was mixed with 0.25 gm fine grain tricalcium phosphate (TCP) (Hitempco Medical Applications, Inc.) by triturating with a spatula, resulting in 5% TCP by weight product. The resulting product was thin and sticky.

EXAMPLE 20

5 gm of the product of Example 18 was mixed with 0.75 gm fine grain tricalcium phosphate (TCP) (Hitempco Medical Applications, Inc.) by triturating with a spatula, resulting in a 15% TCP by weight product. The resulting product was thin and sticky after continued kneading.

EXAMPLE 21

5 gm of the product of Example 18 was mixed with 1.25 gm fine grain tricalcium phosphate (TCP) (Hitempco Medical Applications, Inc.) by triturating with a spatula, resulting in a 25% TCP by weight product. The resulting product was thin and sticky after continued kneading.

EXAMPLE 22

10 gm of Polymer A from Example 2 and 10 gm of Tween® 40 along with a stir bar were added to a clean 100 ml round bottom flask. A static nitrogen gas line was added and the flask was placed in an oil bath at 160° C. for 4 hours. The polymer melted into a liquid which was stirred and then allowed to cool in a dry room overnight. The resulting product exhibited good moldability by hand.

EXAMPLE 23

In a dry room, dried glycolide (7.8 gm), dried ε-caprolactone (69.5 gm), stannous octoate (0.016 gm) as catalyst and dry mannitol (9.1 gm) as initiator were added to a 250 ml round bottom flask that had been dried with nitrogen gas for 24 hours. The flask, containing a mechanical stirrer, was placed in an oil bath at 160° C. and stirred for 24 hours. The contents of the flask were post-treated under vacuum at 73° for 20 hours and placed into a dry room. The polymer was designated Polymer C and had a molecular weight of about 4000.

EXAMPLE 24

In a dry room distilled glycolide (9.08 gm), distilled ε-caprolactone, (81.24 gm) stannous octoate, (0.018 gm) as catalyst and mannitol (8.1 gm) as initiator were added to a 250 ml round bottom flask that had been dried with nitrogen gas for 1 hour. The flask, containing a mechanical stirrer, was placed in an oil bath at 160° C. and stirred for 24 hours. The contents of the flask were placed in a vacuum for 16 hours at 65° C. The polymer was designated Polymer D and had a molecular weight of 4000.

EXAMPLE 25

6.5 gm of Polymer D from Example 24 and 3.5 gm of Pluronic® F68 LF pastille and a stir bar were added to a clean 100 ml round bottom flask. A static nitrogen gas line was added and the contents were dried for 1 hour The flask was placed in a sand bath at 160° C. for 4 hours. The polymers melted into a liquid which was stirred and then placed into a dry room for 48 hours. The resulting product was a hand moldable hard material having 65/35 Polymer D/Pluronic® F68 LF by weight.

EXAMPLE 26

Approximately 1 gm of the product of Example 25 was mixed in a 1:1 ratio by weight with fine grain tricalcium phosphate (TCP) (Hitempco Medical Applications, Inc.). The product and TCP were mixed by triturating with a spatula. The resulting product was a hand moldable hard material after being allowed to stand in a dry room.

EXAMPLE 27

7.5 gm of Polymer D from Example 24 and 2.5 gm of Pluronic® F68 LF pastille and a stir bar were added to a clean 100 ml round bottom flask. A static nitrogen gas line was added and the contents were dried for 30 minutes. The flask was placed in a sand bath at 160° C. for 4 hours. The polymers melted into a liquid which was stirred and then placed into a dry room overnight. The resulting product was a hand moldable hard material having 75/25 Polymer D/Pluronic® F68 LF by weight.

EXAMPLE 28

Approximately 1 gm of the product of Example 27 was mixed in a 1:1 ratio with fine grain tricalcium phosphate (TCP) (Hitempco Medical Applications, Inc.). The product and TCP were mixed by triturating with a spatula. The resulting product was a hand moldable hard material after being allowed to stand in a dry room.

EXAMPLE 29

8.5 gm of Polymer D from Example 24 and 1.5 gm of Pluronic ® F68 LF pastille and a stir bar were added to a clean 100 ml round bottom flask. A static nitrogen gas line was added and the contents were dried for 30 minutes. The flask was placed in a sand bath at 160° C. for 4 hours. The polymers melted into a liquid which was stirred and then placed into a dry room overnight. The resulting product was a hand moldable hard material having 85/15 Polymer D/Pluronic® F68 LF by weight. The product was softer than the product of Example 25 above.

EXAMPLE 30

Approximately 1 gm of the product of Example 29 was mixed in a 1:1 ratio with fine grain tricalcium phosphate (TCP) (Hiretapco Medical Applications, Inc.). The product and TCP were mixed by triturating by hand. The resulting product was a hand moldable hard material after being allowed to stand in a dry room.

EXAMPLE 31

7.0 gm Polymer C from Example 23 and 3.0 gm of Pluronic ® F68 LF pastille and a stir bar were added to a clean 100 ml round bottom flask. A static nitrogen gas line was added and the contents dried for 1 hour. The flask was placed in an oil bath at 160° C. for 4 hours. The polymers melted into a liquid which was stirred and then placed into a dry room overnight. The resulting product was a hand moldable hard material having 70/30 Polymer C/Pluronic® F68 LF by weight.

EXAMPLE 32

Approximately 1 gm of the product of Example 31 was mixed in a 1:1 ratio by weight with fine grain tricalcium phosphate (TCP) (Hitempco Medical Applications, Inc.). The product and TCP were mixed by triturating with a spatula. The resulting product exhibited good moldability by hand.

EXAMPLE 33

6.0 gm of Polymer C from Example 23 and 4.0 gm of Pluronic® F68 LF pastille and a stir bar were added to a clean 100 ml round bottom flask. A static nitrogen gas line was added and the contents dried for 2 hours. The flask was placed in a sand bath at 160° C. for 4 hours. The polymers melted into a liquid which was stirred and then placed into a dry room for 48 hours. The resulting product was a hand moldable hard material having 60/40 Polymer C/Pluronic® F68 LF by weight.

EXAMPLE 34

Approximately 1 gm of the product of Example 33 was mixed in a 1:1 ratio by weight with fine grain tricalcium phosphate (TCP) (Hitempco Medical Applications, Inc.). The product and TCP were mixed by triturating with a spatula. The resulting product exhibited good moldability by hand.

EXAMPLE 35

Approximately 1 gm of the product of Example 33 was mixed in a 1:2 ratio by weight with fine grain tricalcium phosphate (TCP) (Hitempco Medical Applications, Inc.). The product and TCP were mixed by triturating with a spatula. The resulting product exhibited good moldability by hand. When compared to the product of Example 34 above, it was slightly harder and less sticky.

EXAMPLE 36

Approximately 1 gm of the product of Example 33 was mixed in a 1:3 ratio by weight with fine grain tricalcium phosphate (TCP) (Hiretapco Medical Applications, Inc.). The product and TCP were mixed by triturating with a spatula. The resulting product exhibited good moldability by hand. When compared to the product of Example 34 above, it was slightly harder and less sticky.

EXAMPLE 37

Approximately 2 gm of Polymer C from Example 23 was mixed in a 1 ratio by weight with fine grain tricalcium phosphate (TCP) (Hitempco Medical Applications, Inc.). The polymers and TCP were mixed by triturating with a spatula. The resulting product was moldable by hand and sticky.

EXAMPLE 38

Approximately 2 gm of Polymer C from Example 23 was mixed in a 2 ratio by weight with fine grain tricalcium phosphate (TCP) (Hitempco Medical Applications, Inc.). The polymer and TCP were mixed by triturating with a spatula. The resulting product was moldable by hand and slightly sticky.

EXAMPLE 39

Approximately 2 gm of Polymer D from Example 24 was mixed in a 1 ratio by weight with tricalcium phosphate (TCP) (Hitempco Medical Applications, Inc.). The polymer and TCP were mixed by triturating with a spatula. The resulting product was initially hard but moldable by hand and became softer after continued kneading.

EXAMPLE 40

Approximately 2 gm of Polymer D from Example 24 was mixed in a 1:2 ratio by weight with tricalcium phosphate (TCP) (Hitempco Medical Applications, Inc.). The polymer and TCP were mixed by triturating with a spatula. The resulting product was moldable by hand and was slightly harder and less sticky than the product of Example 39 above.

EXAMPLE 41

10 gm of Polymer A from Example 2 and 6.67 gm of Pluronic®L 122 and a mechanical stirrer were added to a dry 100 ml round bottom flask. The flask and contents were dried overnight under static nitrogen gas. The flask was placed in a sand bath at 160° C. and stirred for 8 hours. The resulting product was non-homogeneous and was placed in a dry room for 24 hours. The product did not harden.

EXAMPLE 42

10 gm of Polymer A from Example 2 and 6.67 gm of Pluronic®L64 and a mechanical stirrer were added to a dry 100 ml round bottom flask. The flask and contents were dried overnight under static nitrogen gas. The flask was placed in a sand bath at 160° C. and stirred for 4 hours. The resulting product was 60/40 Polymer A/Pluronic® L64 by weight and was homogeneous and a hand moldable hard material.

EXAMPLE 43

2 gm of product from Example 42 was mixed in a 1:1 ratio with tricalcium phosphate (TCP) (Hitempco Medical Applications, Inc.). The product and TCP were mixed by triturating with a spatula. The resulting product was moldable by hand.

EXAMPLE 44

10.5 gm of Polymer A from Example 2 and 4.5 gm of Pluronic® L64 and a mechanical stirrer were added to a dry 100 ml round bottom flask. A static nitrogen gas line was added and the contents were dried for 1 hour. The flask was placed in a sand bath at 160° for 4 hours. The polymer melted into a liquid which was stirred and then placed in a dry room for 24 hours. The resulting product was a hand moldable hard material having 70/30 Polymer A/Pluronic® L64 by weight.

EXAMPLE 45

2 gm of product from Example 44 was mixed in a 1: 1 ratio with tricalcium phosphate (TCP) (Hitempco Medical Applications, Inc.). The product and TCP were mixed by triturating with a spatula. The resulting product was superiorly moldable and workable by hand.

EXAMPLE 46

9.75 gm of Polymer A from Example 2 and 5.25 gm Pluronic® L64 and a mechanical stirrer were placed in a clean 100 ml round bottom flask. A static nitrogen gas line was added and the contents were dried for 1 hour. The flask was placed in a sand bath at 160° for 5 hours. The polymer melted into a liquid which was stirred and then placed in a dry room overnight. The resulting product was a hand moldable hard material having 65/35 Polymer A/Pluronic® L64 by weight.

EXAMPLE 47

2 gm of product from Example 46 was mixed in a 1:1 ratio with tricalcium phosphate (TCP) (Hitempco Medical Applications, Inc.). The product and TCP were mixed by triturating with a spatula. The resulting product was superiorly moldable and workable by hand.

EXAMPLE 48

3.5 of Polymer A from Example 2 and 6.5 gm Pluronic® L64 and a mechanical stirrer were placed in a clean 100 ml round bottom flask. A static nitrogen gas line was added and the contents were dried for 1 hour. The flask was placed in a sand bath at 160° C. for 4 hours. The polymer melted into a liquid which was stirred and then placed in a dry room overnight. The resulting product did not mix well and was non-homogeneous.

EXAMPLE 49

7.0 gm of Polymer B from Example 11 and 7.0 gm of Pluronic® F77 and a stir bar were added to a clean 100 ml round bottom flask. A static nitrogen gas line was added and the contents were dried for 1 hour. The flask was placed in a sand_bath at 160° C. for 4 hours. The polymers melted into a liquid which was stirred and then placed into a dry room for 24 hours. The resulting product was a hand moldable hard material.

EXAMPLE 50

7.0 gm of Polymer C from Example 23 and 7.0 gm of Pluronic® F77 and a stir bar are added to a clean 100 ml round bottom flask. A static nitrogen gas line is added and the contents are dried for 24 hours. The flask is placed in an oil bath at 160° C. for 4 hours. The polymers melt into a liquid which is stirred and then placed into a dry room for 24 hours. The resulting material is moldable and workable by hand.

EXAMPLE 51

8.0 gm of Polymer C from Example 23 and 2.0 gm of Pluronic® F68 LF pastille and a stir bar were added to a clean 100 ml round bottom flask. The flask was placed in an oil bath at 160° C. for 4 hours under static nitrogen gas. The polymers melted into a liquid which was stirred and then placed in a dry room overnight. The resulting product was a hand moldable hard material having 80/20 Polymer C/Pluronic® F68 by weight.

EXAMPLE 52

2 gm of the product of Example 51 was mixed in a 1: 1 ratio with fine grain tricalcium phosphate (TCP) (Hitempco Medical Applications, Inc.). The product and TCP were mixed by triturating with a spatula. The resulting material was slightly thin and sticky. After standing in a dry room for 24 hours the material became harder and less sticky and exhibited good hand moldability.

EXAMPLE 53

7 gm of Polymer C from Example 23 and 3 gm of Pluronic® F68 CS and a stir bar were added to a clean 100 ml round bottom flask. The flask was placed in an oil bath at 160° C. for 4 hours under static nitrogen gas. The polymer melted into a liquid which was stirred and then placed in a dry room for 24 hours. The resulting material was hard and not moldable by hand, having 70/30 Polymer C/Pluronic F68 CS by weight.

EXAMPLE 54

A portion of the product of Example 34 above (60/40 Polymer C/Pluronic® F68 LF mixed 1:1 with tricalcium phosphate) was used to stop bleeding of a tibial bone defect in a dog. The product was kneaded by hand and applied to the defect. Bleeding stopped, but the product disbanded and bleeding resumed.

EXAMPLE 55

A portion of the product of Example 32 above, (70/30 Polymer C/Pluronic® F68 LF mixed 1:1 with tricalcium phosphate) was used to stop bleeding of the same tibial bone defect in the dog from Example 54 above. The product was kneaded by hand and applied over residual disbanded product left from Example 54 above. Bleeding stopped but some of the applied product disbanded. 100 minutes later the defect was reexamined and inconsistent topography was noted.

EXAMPLE 56

A portion of the product of Example 52 above, (80/20 Polymer C/Pluronic® F68 mixed 1:1 with tricalcium phosphate) was used to stop bleeding of a tibial bone defect in a dog. The product was kneaded by hand and applied to the defect. Bleeding stopped. The product was easy to apply and did not disband. 100 minutes later the defect was reexamined and the product was coherent and there was no bleeding at the defect.

It will be understood that various modifications may be made to the embodiments disclosed herein. For example, the above-described mixing temperatures and melting times may be varied depending on the composition of the mixture. Therefore, the above description should not be construed as limiting, but merely as exemplifications of preferred embodiments. Those skilled in art will envision other modifications within the scope and spirit of the claims appended hereto.

What is claimed is:

1. A hand moldable biodegradable surgical material comprising a blend of a bioabsorbable polymer and a surface active agent selected from the group consisting of sorbitan fatty acid ester and poly(oxypropylene)/poly(oxyethylene) block copolymer and a leaching agent selected from the group consisting of calcium carbonate, calcium chloride, tricalcium phosphate and hydroxyapatite wherein the leaching agent is present in an amount ranging from about 1 percent to about 70 percent by weight of the material.

2. A hand moldable biodegradable surgical material according to claim 1 wherein the bioabsorbable polymer is derived from a member selected from the group consisting of hydroxyacids, lactones, carbonates, etheresters, anhydrides, esteramides, orthoesters, and copolymers, terpolymers and blends thereof.

3. A hand moldable biodegradable surgical material according to claim 2 wherein the bioabsorbable polymer is selected from the group consisting of polylactide, polyglycolide, polydioxanone, polycaprolactone, polytrimethylene carbonate and copolymers, terpolymers and blends thereof.

4. A hand moldable biodegradable surgical material according to claim 3 wherein the bioabsorbable polymer is a star polymer of glycolide and caprolactone.

5. A hand moldable biodegradable surgical material according to claim 4 wherein glycolide is present in an amount of about 9.8 weight percent and caprolactone is present in an amount of about 90.2 weight percent.

6. A hand moldable biodegradable surgical material according to claim 1 wherein the sorbitan fatty acid ester is present in an amount ranging from about 10 weight percent to about 90 weight percent.

7. A hand moldable biodegradable surgical material according to claim 1 wherein the sorbitan fatty acid ester is polyoxyethylene sorbitan fatty acid ester.

8. A hand moldable biodegradable surgical material according to claim 7 wherein the polyoxyethylene sorbitan fatty acid ester is polyoxyethylene sorbitan monopalmitate.

9. A hand moldable biodegradable surgical material according to claim 1 wherein the bioabsorbable polymer is a star polymer of glycolide and caprolactone and the sorbitan fatty acid ester is polyoxyethylene sorbitan monopalmitate.

10. A hand moldable biodegradable surgical material according to claim 1 wherein the poly(oxypropylene)poly(oxyethylene) block copolymer is present in an amount ranging from about 2 weight percent to about 55 weight percent.

11. A hand moldable biodegradable surgical material according to claim 1 wherein the bioabsorbable material is a star polymer of glycolide and caprolactone and the poly(oxypropylene)poly(oxyethylene) block copolymer has a molecular weight of about 7500.

12. A method of effecting hemostasis comprising providing a moldable biodegradable surgical material according to claim 1 and applying the material to a suitable locus.

13. A method of producing a hand moldable biodegradable surgical material comprising providing a bioabsorbable polymer and blending the bioabsorbable polymer with a surface active agent selected from the group consisting of sorbitan fatty acid ester and poly(oxypropylene)/poly(oxyethylene) block copolymer, and a leaching agent selected from the group consisting of calcium carbonate, calcium chloride, tricalcium phosphate and hydroxyapatite wherein the leaching agent is present in an amount ranging from about 1 percent to about 70 percent by weight of the material.

14. A hand moldable biodegradable surgical material comprising a blend of bioabsorbable polymer and a leaching agent selected from the group Consisting of calcium carbonate, calcium chloride, tricalcium phosphate and hydroxyapatite wherein the leaching agent is present in an amount ranging from about 1 percent to about 70 percent by weight of the material.

15. A hand moldable biodegradable surgical material according to claim 1 wherein the bioabsorbable polymer is derived from a member selected from the group consisting of hydroxyacids, lactones, carbonates, estheresters, anhydrides, esteramides, orthoesters, and copolymers, terpolymers and blends thereof.

16. A hand moldable biodegradable surgical material according to claim 14, wherein the bioabsorbable polymer is a star polymer of glycolide and caprolactone and the leaching agent is tricalcium phosphate.

* * * * *